(12) United States Patent
Annis et al.

(10) Patent No.: US 8,222,250 B2
(45) Date of Patent: Jul. 17, 2012

(54) BIOCIDAL COMPOSITIONS

(75) Inventors: Ioana Annis, Mundelein, IL (US);
Suzanne DeBruhl, Kenosha, WI (US);
Heidie M. Jevey, Glen Ellyn, IL (US);
Jon B. Raymond, Buffalo Grove, IL (US)

(73) Assignee: Dow Global Technologies LLC, Midland, MI (US)

( * ) Notice: Subject to any disclaimer, the term of this patent is extended or adjusted under 35 U.S.C. 154(b) by 287 days.

(21) Appl. No.: 12/492,470

(22) Filed: Jun. 26, 2009

(65) Prior Publication Data

US 2009/0325965 A1 Dec. 31, 2009

Related U.S. Application Data

(60) Provisional application No. 61/076,262, filed on Jun. 27, 2008.

(51) Int. Cl.
*A01N 43/66* (2006.01)
*A01P 1/00* (2006.01)
(52) U.S. Cl. .................................... 514/244
(58) Field of Classification Search ................... 514/244
See application file for complete search history.

(56) References Cited

U.S. PATENT DOCUMENTS

| | | | |
|---|---|---|---|
| 3,908,009 A | | 9/1975 | Polemenakos et al. |
| 5,302,406 A | * | 4/1994 | Ludwig et al. ................ 426/281 |
| 5,464,850 A | | 11/1995 | Voo et al. |
| 5,637,587 A | * | 6/1997 | Gross et al. .................. 514/244 |
| 6,114,366 A | | 9/2000 | Lutz et al. |
| 6,121,302 A | | 9/2000 | Rothenburger et al. |
| 6,133,300 A | | 10/2000 | Smith et al. |
| 6,576,633 B1 | | 6/2003 | Young et al. |
| 2003/0050280 A1 | | 3/2003 | Sweeny et al. |
| 2006/0106024 A1 | | 5/2006 | Levy et al. |
| 2007/0202177 A1 | | 8/2007 | Hoang |

FOREIGN PATENT DOCUMENTS

| | | |
|---|---|---|
| EP | 1665933 B1 | 9/2007 |
| JP | 2004231896 | 8/2004 |
| WO | 9730588 A1 | 8/1997 |

OTHER PUBLICATIONS

International Search Report and Written Opinion for PCT/US2009/048791 dated Jun. 29, 2010.
Izzat et al., "Effects of edta on the antimicrobial properties of mixtures of cutting fluid preservatives", Tribology International, 1981, 171-173, IPC Business Press.

* cited by examiner

*Primary Examiner* — Shengjun Wang
*Assistant Examiner* — Sahar Javanmard

(57) ABSTRACT

Compositions of 1-(3-chloroallyl)-3,5,7-triaza-1-azonia-adamantane chloride, and an optional second biocide, in copolymers of ethylene oxide/propylene oxide are provided. The compositions exhibit good color and phase stability.

11 Claims, No Drawings

BIOCIDAL COMPOSITIONS

CROSS-REFERENCES TO RELATED APPLICATIONS

This application claims benefit of priority from U.S. Provisional Patent Application No. 61/076,262 filed Jun. 27, 2008, which provisional application is hereby incorporated by reference in its entirety.

FIELD OF THE INVENTION

The invention relates to compositions of the biocidal compound 1-(3-chloroallyl)-3,5,7-triaza-1-azonia-adamantane chloride. The compositions are color and phase stable.

BACKGROUND OF THE INVENTION

The compound 1-(3-chloroallyl)-3,5,7-triaza-1-azonia-adamantane chloride (CTAC) is a well established biocidal agent that is particularly effective in aqueous dispersions and emulsions. It is known, however, that when CTAC is used in clear or light-colored aqueous formulations, the formulation visibly yellows on aging. This is an undesirable phenomenon, especially for the cosmetics, paints, and coatings industries.

CTAC can be blended with other biocidal compounds to increase its efficacy. For instance, blends of CTAC and 1,2-benzisothiazolin-3-one (BIT) have been observed to provide a synergistic effect under certain concentration ratios. That is, the combined materials result in improved biocidal properties than would otherwise be expected based on their individual performance at the particular use-concentration. The observed synergy permits reduced amounts of the materials to be used to achieve acceptable biocidal properties. Biocidal formulations of CTAC with a second biocide, such as BIT, are therefore highly desirable.

Difficulties can arise, however, in formulating CTAC with a second biocide into a stable blend, particularly where the two agents have differing physical and/or chemical compatibilities. This is the case, for instance, with CTAC and BIT. Such formulations tend to phase separate. Blend stability, however, is an important attribute of such formulations as it impacts the handling and storage of the materials as well as inventory and transportation costs.

The tendency of CTAC to discolor upon aging and the difficulty of formulating CTAC with other biocides into color and phase stable blends are significant limitations of currently known systems.

BRIEF SUMMARY OF THE INVENTION

The invention addresses the problem of color and phase stability of CTAC compositions and blends of CTAC with other biocides. In particular, the invention formulates such materials in certain dispersants. The formulations can then be readily utilized in various media, including aqueous systems.

The invention, therefore, provides a composition comprising: 1-(3-chloroallyl)-3,5,7-triaza-1-azonia-adamantane chloride; and a dispersant comprising a copolymer of ethylene oxide and propylene oxide.

According to a preferred embodiment, the composition further comprises a second biocide. A particularly preferred second biocide is BIT.

DETAILED DESCRIPTION OF THE INVENTION

The inventors have discovered that by formulating CTAC with the dispersants described herein, compositions are achieved that exhibit acceptable storage stability, including color and phase stability over extended periods of time. As a result, the compositions of the invention address the handling and storage issues that are usually observed with CTAC and CTAC/second biocide blends. Advantageously, therefore, the compositions of the invention can reduce the inventory and transportation costs associated with such materials.

According to the invention, the biocidal composition comprises CTAC and a dispersant comprising a copolymer of ethylene oxide and propylene oxide. The CTAC compound may be the cis isomer, the trans isomer, or a mixture of cis and trans isomers. Preferably, it is the cis isomer or a mixture of the cis and trans isomers. The concentration of CTAC in the composition is preferably between about 0.1 and 50 percent by weight, more preferably between about 5 and 30 percent by weight.

The dispersant used in the compositions of the invention is a copolymer of ethylene oxide and propylene oxide. The copolymer may be block, segmented, or random. Preferred dispersants include copolymers of the formula (I):

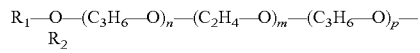

where $R_1$ and $R_2$ are independently H, aryl, branched or linear $C_1$-$C_{18}$ alkyl; or $R_1$ or $R_2$ together with the oxygen to which each is attached independently forms an acrylate, an alkylene glycol such as dipropylene glycol methyl ether, or a linear or branched $C_1$-$C_6$ alkyl ester; and m, n, and p are independently from 1-1000.

Preferred copolymers of formula I, here designated as having formula I-1, include materials where $R_1$ is H or linear or branched $C_1$-$C_6$ alkyl, more preferably H or $C_1$-$C_3$ alkyl, and even more preferably H.

Preferred copolymers of formula I or formula I-1, here designated as having formula I-2, also include materials in which $R_2$ is H or linear or branched $C_1$-$C_6$ alkyl, more preferably H or $C_1$-$C_3$ alkyl, and even more preferably H.

Preferred copolymers of formula I, I-1, or I-2, here designated as having formula I-3, include materials in which m is between about 1 and 500, more preferably between about 10 and 300, and even more preferably, between about 10 and 80.

Preferred copolymers of formula I, I-1, I-2, or I-3, here designated as having formula I-4, include materials in which n is between about 1 and 800, more preferably between about 10 and 500, and even more preferably, between about 10 and 100.

Preferred copolymers of formula I, I-1, I-2, I-3, or I-4, here designated as having formula I-5, include materials in which p is between about 1 and 800, more preferably between about 10 and 500, and even more preferably, between about 10 and 100.

Particularly preferred copolymers of formula I, I-1, I-2, I-3, I-4, or I-5 are materials of the class poly(propylene glycol)-block-poly(ethylene glycol)-block-poly(propylene glycol), here designated as having formula I-6.

Preferably, the number average molecular weight of the dispersant copolymers of formulae I, I-1, I-2, I-3, I-4, I-5, or I-6 is in the range of between about 200 and about 20,000, more preferably between about 1,000 and 10,000. In some preferred embodiments, the ethylene oxide content of the polymers is between about 10 and 80 mole percent, more preferably between about 20 and 50 mole percent.

According to a preferred embodiment, the compositions of the invention also contain an optional carrier. The carrier aids in further improving the stability of the compositions. Preferably, the carrier is an alkylene glycol compound. Particularly suitable are carriers of the following formula II:

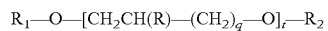

where $R_1$ and $R_2$ are as defined above for polymers of formula I;

R is H or $C_1$-$C_3$ alkyl (preferably $CH_3$);
t is 1 to 50 units; and
q is 0, 1, or 2.

Preferred carriers of formula II, here designated as having formula II-1, include compounds in which $R_1$ is H or linear or branched $C_1$-$C_6$ alkyl, more preferably H or $C_1$-$C_3$ alkyl, and even more preferably H.

Preferred carriers of formula II or formula II-1, here designated as having formula II-2, also include materials in which $R_2$ is H or linear or branched $C_1$-$C_6$ alkyl, more preferably H or $C_1$-$C_3$ alkyl, and even more preferably H.

Preferred carriers of formula II, II-1, or II-2, here designated as having formula II-3, include materials in which t is between about 1 and 40, more preferably between about 1 and 20, and even more preferably, between about 2 and 10.

Preferred carriers of formula II, II-1, II-2, and II-3, here designated as having formula II-4, include compounds in which q is 0 and R is H.

Preferred carriers of formula II, II-1, II-2, and II-3, here designated as having formula II-5, include compounds in which q is 0 and R is $CH_3$.

Preferred carriers of formula II, II-1, II-2, and II-3, here designated as having formula II-6, include compounds in which q is 2 and R is H.

Preferred carriers of formula II, II-1, II-2, and II-3, here designated as having formula II-7, include compounds in which q is 1 and R is H.

Preferably, the number average molecular weight of the carriers of formulae II, II-1, II-2, II-3, II-4, II-5, II-6, or II-7 is in the range of between about 60 and about 5000, more preferably between about 60 and 1000, and even more preferably between about 200 and about 800.

Non-limiting examples of suitable carriers of formula II include: ethylene glycol, methoxyethanol, diethylene glycol butyl ether, diethylene glycol methyl ether, phenoxyethanol, polyethylene glycols of molecular weights up to 1000, mono- or di-ethercapped polyethylene glycols, such as methoxy-PEG, butoxy-PEG, propylene glycol, 1-methoxy-2-propanol, propylene glycol diacetate, propylene glycol butyl ether, 1-phenoxy-2-propanol, dipropylene glycol methyl ether, dipropylene glycol dimethyl ether, dipropylene glycol methyl ether acetate, tripropylene glycol methyl ether, poly(propylene glycol) of MW up to 5000; poly(propylene glycol) acrylate; poly(propylene glycol) acetate; poly(propylene glycol) monobutyl ether, Butylene glycol, poly(butylene glycol), and mono- and diethers of poly(butylene glycol).

A particularly preferred carrier is polypropylene glycol with a number average molecular weight range of 200 to 600, more preferably 300 to 500.

When used, the concentration of carrier in the composition is preferably between about 10 and 90 percent by weight, more preferably between about 50 and 80 percent by weight.

The compositions of the invention may also contain an optional thickener to facilitate handling and/or compatibility of the composition with various media. The thickener is preferably a polyalkylene glycol polymer, more preferably polyethylene glycol, and preferably has a number average molecular weight ranging from about 200 to about 100,000, more preferably from about 200 to about 20,000 and even more preferably from about 200 to about 5,000. When used, the concentration of the thickener in the composition is advantageously between about 0.1 to about 10 percent by weight, more preferably between about 1 and 5 percent by weight.

In a preferred embodiment, the compositions of the invention contain a second biocide. It has been found that dispersants and optional carriers described herein provide CTAC/second biocide compositions that are phase and color stable. Suitable second biocides for this embodiment include BIT, 5-chloro-2-methyl-3(2H)-isothiazolone and 2-methyl-3(2H)-isothiazolone mixtures (CMIT/MIT) or the individual actives, glutaraldehyde, 3-iodo-2-propynyl butyl carbamate (IPBC), octyl isothiazolinone (OIT), dichlorooctylisothiazolinone (DCOIT), 2-bromo-2-nitro-1,3-propanediol (bronopol), and 2,2-dibromo-3-nitrilopropionamide (DBNPA), bromonitrostyrene (BNS), chlorothalonil, β tubulin inhibitors such as carbendazim and thiabendazole, diiodomethyl-p-tolylsulfone (DIMTS), triazine-based biocides such as terbutryn, cybutryn, and prometryn, dimethylurea-based biocides such as diuron, isoproturon, chlorotuloron, and flumeturon, azoles such as propiconazole, difenoconazole, cyproconazole, and tebuconazole, 2-(thiocyanomethylthio)benzothiazole (TCMTB), pyrithiones such as zinc pyrithione, formaldehyde-releasing biocides, acetaldehyde-releasing biocides such as 2,6-dimethyl-m-dioxan-4-ol acetate, phenolic biocide such as ortho-phenyl phenol and Triclosan. Particularly suitable is BIT. Preferably, the concentration of second biocide in this preferred embodiment is between about 0.1 and 50 weight percent, more preferably between about 1 and 30 weight percent.

The dispersants, carriers, and thickeners used in the compositions of the invention can be readily prepared by a person of ordinary skill in the art using standard techniques, and/or are commercially available. For instance, ethylene oxide/propylene oxide copolymer dispersants are available from The Dow Chemical Company as Tergitol™ L products, or from BASF as Pluronic® R products. Various alkylene glycols, useful as carriers or thickeners, are also available from The Dow Chemical Company, including polyethylene glycols (e.g., Carbowax PEG 8000, a polymer with a molecular weight in the range of 7000 to 9000 well suited for use as a thickener), methoxypolyethylene glycols (e.g., Carbowax MPEGs), and various propylene glycols (e.g., Polyglycol P425, a polypropylene glycol with a molecular weight of about 425 well suited for use as a carrier).

Other additives may optionally be included in the compositions of the invention such as, for instance, further additional biocides (such as one or more of 3-iodo-2-propynylbutylcarbamate (IPBC), diiodomethyl-para-tolylsulfone (DIMTS, Amical®), 2-n-octyl-4-isothiazolin-3-one (OIT), 2,2-dibromo-2-nitrilopropionamide (DBNPA), bromonitrostyrene (BNS), other formaldehyde releasers, bronopol, or ortho-phenylphenol (OPP)), chelating agents, dyes, perfumes, specialized dispersing agents, antioxidants, and other thickeners such as hydrophobic silica and bentonite.

The compositions of the invention can be readily prepared by techniques well known in the art. For instance, the biocide(s) and any other solid additives may be milled and then dispersed in the dispersant (and optional carrier and thickener) under high speed agitation. Milling is not required, however, and the solids may be directly dispersed in the dispersant under high speed agitation.

A particularly preferred composition according to the invention comprises: 1-(3-chloroallyl)-3,5,7-triaza-1-azonia-adamantane chloride; 1,2-benzisothiazolin-3-one; a dispersant comprising a copolymer of ethylene oxide and propylene oxide; a carrier comprising an alkylene glycol compound; and an optional thickener.

The dispersant of this preferred embodiment is preferably any of the dispersants of formulae I, I-1, I-2, I-3, I-4, I-5, or I-6 described above. Most preferably, the dispersant is a copolymer of formula: poly(propylene glycol)-block-poly(ethylene glycol)-block-poly(propylene glycol).

The carrier in this preferred embodiment is preferably any of the carriers of formulae II, II-1, II-2, II-3, II-4, II-5, or II-6 as described above. Most preferably, the carrier is an alkylene glycol of formula II in which R is $CH_3$, $R_1$ and $R_2$ are each H and q is 0. Also preferably, the number average molecular weight is between about 60 and about 1000.

When used, the thickener in this preferred embodiment is preferably polyethylene glycol with a number average molecular weight of between about 200 and about 10,000, more preferably between about 200 and 5000.

In the foregoing preferred embodiment, the concentrations of components are advantageously as follows:
- 0.1 to 50, more preferably 10 to 30, percent by weight of 1-(3-chloroallyl)-3,5,7-triaza-1-azonia-adamantane chloride;
- 0.1 to 40, more preferably 2 to 15, percent by weight of 1,2-benzisothiazolin-3-one;
- 0.1 to 20, more preferably 1 to 10, percent by weight of the dispersant;
- 0 to 20, more preferably 0.1 to 5, percent by weight of the optional thickener; and balance carrier.

According to a further preferred aspect, the weight ratio of BIT to CTAC in the foregoing embodiment is 1:4 to 4:1. Also preferably, the BIT:CTAC weight ratio is from 1:2 to 2:1 or, further, it is 1:1. Within these ratios, the BIT:CTAC combination demonstrates synergistic biocidal efficacy.

The compositions of the invention can be used in various media where biocidal activity is desired. Preferably the compositions are used for in-can preservation or to provide a combination of in-can preservation and dry-state antifungal properties. Examples of suitable media include, without limitation, paints and coatings, emulsion polymers and latexes, surfactants, metal working fluids, cleaners, detergents, household products, agricultural products, and leather product. Although useable in aqueous media, the compositions of the invention themselves are preferably non aqueous. By non-aqueous is meant that the composition, prior to addition to the media, have a water content of 10 weight percent or less, more preferably 3 weight percent or less.

A sufficient amount of the composition is used in the media to provide biocidal efficacy. While this amount will vary based on various factors, such as the nature of the media, the organisms to be controlled and the like, the amount can readily be determined by a person of ordinary skill in the art without undue experimentation. By way of example, for in-can preservation, an amount of the composition is typically used so as to provide a final biocide(s) concentration of between about 0.001% and 0.5%.

The following examples are illustrative of the invention but are not intended to limit its scope.

EXAMPLES

Materials

Polyglycol P425: a polypropylene glycol with a molecular weight of about 425 used as a carrier. Available from The Dow Chemical Company.

MPEG 350: A methoxypolyethylene glycol with an average molecular weight range of 335 to 365 used as a carrier in the invention. Available from The Dow Chemical Company.

Tergitol L62: a copolymer with the general structure poly(ethylene oxide)/poly(propylene oxide)/poly(ethylene oxide) and average MW of about 2500 available from The Dow Chemical Company used in the formulation as a dispersant.

Tergitol L64: a copolymer with the general structure poly(ethylene oxide)/poly(propylene oxide)/poly(ethylene oxide) and average MW of about 2900 available from The Dow Chemical Company used in the invention as a dispersant.

Pluronic 25R4: a copolymer with the general structure poly(propylene oxide)/poly(ethylene oxide)/poly(propylene oxide) with an average molecular weight of about 3600, used in the invention as a dispersant. Available from BASF.

Tergitol NP9: A nonylphenol ethoxylate based surfactant used for comparison to the ethylene oxide/propylene oxide dispersants of the invention. Available from The Dow Chemical Company.

Tergitol NP13: A nonylphenol ethoxylate based surfactant used for comparison to the ethylene oxide/propylene oxide dispersants of the invention. Available from The Dow Chemical Company.

Tergitol NP40: A nonylphenol ethoxylate based surfactant used for comparison to the ethylene oxide/propylene oxide dispersants of the invention. Available from The Dow Chemical Company.

Dowicil 200: 96% cis 1-(3-chloroallyl)-3,5,7-triaza-1-azoniaadamantane chloride available from The Dow Chemical Company.

Example 1

In a glass beaker is added 51.2 g of Polyglycol P425, 5.25 g of Pluronic 25R4 and 2.47 g of PEG 6000. The mixture is heated to 60° C. with agitation to facilitate homogenization. To the homogenized clear mixture is added 4.12 g of BIT paste (85% active) and 7.0 g of Dowicil 200, and the mix is placed into a quickie ball mill. The mill is placed on a paint shaker and homogenized for 30 min. After that the white dispersion is discharged, and studied. The dispersion shows no change in color after 2 month storage at 40° C., and no phase separation after 5 cycles of freeze-thaw testing.

Example 2

In a glass beaker is added 51.1 g of Polyglycol P425, 5.27 g of Tergitol L62 and 2.45 g of PEG 6000. The mixture is heated to 60° C. with agitation to facilitate homogenization. To the homogenized clear mixture is added 4.12 g of BIT paste (85% active) and 7.0 g of Dowicil 200, and the mix is placed into a quickie-ball mill. The mill is placed on a paint shaker and homogenized for 15 min. After that, the white dispersion is discharged, and studied. The dispersion shows no change in color after 2 month storage at 40° C., and less than 5% of the final volume phase separation after storage at 40° C. for 2 weeks.

Example 3

In a glass beaker is added 65.96 g of MPEG 350, 11.01 g of Tergitol L62 and 1.11 g of PEG 6000. The mixture is heated to 60° C. with agitation to facilitate homogenization. To the homogenized clear mixture is added 6.40 g of BIT paste (85% active) and 7.51 g of Dowicil 200, and the mix is placed into a quickie-ball mill. The mill is placed on a paint shaker and homogenized for 15 min. After that, the white dispersion is discharged, and studied. The dispersion shows no change in color after 2 month storage at 40° C., and less than 10% of the final volume phase separation after storage for 3 days.

Example 4

In a glass beaker is added 204.70 g of Polyglycol P425, 21.10 g of Tergitol L64 and 9.86 g of PEG 8000. The mixture is heated to 60° C. with agitation to facilitate homogenization. To the homogenized clear mixture is added 16.81 g of BIT paste (85% active) and 28.050 g of Dowicil 200, and the mix is placed into a quickie ball mill. The mill is placed on a paint shaker and homogenized for 30 min. After that the white dispersion is discharged, and studied. The dispersion shows no change in color, and only 6% phase separation after 6 weeks storage at 40° C.

Example 5

In a quickie ball mill is added 77.99 g of Polyglycol P425, 7.34 g of BIT Paste, 9.77 g of Dowicil 200 and 3.91 g of Tergitol L62. The mill is placed on a paint shaker and homogenized for 15 min. After that, the white dispersion is discharged, and studied. Less than 8% of the final volume of the dispersion shows phase separation after spinning it in a centrifuge for 2 minutes at 2000 rpm Example 6

Comparative

In a glass beaker is added 65.96 g of MPEG 350, 11.01 g of Tergitol NP9 and 1.11 g of PEG 6000. The mixture is heated to 60° C. with agitation to facilitate homogenization. To the homogenized clear mixture is added 6.42 g of BIT paste (85% active) and 7.52 g of Dowicil 200, and the mix is placed into a quickie-ball mill. The mill is placed on a paint shaker and homogenized for 15 min. After that, the white dispersion is discharged, and studied. The dispersion shows no change in color, and less than 8% of the final volume suffers phase separation after storage for 3 days.

Examples 7-12

Examples 7-12 are shown in Table 1. The compositions are prepared essentially as described in Examples 1-6 above.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A biocidal composition comprising:
   1-(3-chloroallyl)-3,5,7-triaza-1-azonia-adamantane chloride; and
   a dispersant comprising a copolymer of ethylene oxide and propylene oxide as a color and phase stabilizer for the 1-(3-chloroallyl)-3,5,7-triaza-1-azonia-adamantane chloride;
   a carrier comprising a mono-ether capped polyethylene glycol compound or a polypropylene glycol compound; and
   a thickener comprising a polyethylene glycol compound.

2. A biocidal composition according to claim 1 further comprising a second biocide.

3. A biocidal composition according to claim 1 wherein the carrier has a number average molecular weight of between about 60 and 5000.

4. A biocidal composition according to claim 1 wherein the thickener has a number average molecular weight between about 200 and 100,000.

5. A biocidal composition according to claim 1 wherein the thickener has a number average molecular weight between about 200 and 5000.

6. A biocidal composition according to claim 2 wherein the second biocide is 1,2-benzisothiazolin-3-one.

7. A biocidal composition comprising:
   1-(3-chloroallyl)-3,5,7-triaza-1-azonia-adamantane chloride;

TABLE 1

| Ex. # | Biocide 1 (wt %) | Biocide 2 (wt %) | Glycol Carrier (wt %) | Surfactant (wt %) | Thickener (wt %) | Observations |
|---|---|---|---|---|---|---|
| 7. | BIT (7.6%) | CTAC (15) | polypropylene glycol[1] (65) | EO/PO copolymer[2] (7.5) | PEG 8000 (3.5) | No phase separation after 6 wks at 40° C. |
| 8 | BIT (7.5) | CTAC (15%) | polypropylene glycol[1] (65.1) | EO/PO copolymer[4] (7.5) | PEG 8000 (3.6) | <4% separation after 6 weeks at 40° C. |
| 9 (Comparative) | BIT (7.4%) | CTAC (9.75) | MPEG 350 (78) | Nonylphenol Ethoxylate[5] (4) | — | <13% phase separation after spinning for 2 min at 2000 rpm |
| 10 | BIT (7.4) | CTAC (9.8) | Tripropylene glycol methyl ether (78) | EO/PO copylmer[2] (3.9) | — | <32% phase separation after spinning for 2 min at 2000 rpm |
| 11 (Comparative) | — | CTAC (10.2) | polypropylene glycol[1] (81.6) | Nonylphenol Ethoxylate[6] (4) | — | <11% separation after 3 days at ambient conditions |
| 12 (Comparative) | BIT (6.6) | CTAC (8.8) | polypropylene glycol[1] (84.5) | Nonylphenol Ethoxylate[3] (14.1) | PEG 6000 (1.4) | <39% separation after 4 weeks at ambient conditions |

[1]Polyglycol P425;
[2]Tergitol L62;
[3]Tergitol NP9;
[4]Pluronic 25R4;
[5]Tergitol NP13;
[6]Tergitol NP40

1,2-benzisothiazolin-3-one;
a dispersant comprising a copolymer of ethylene oxide and propylene oxide as a color and phase stabilizer for the 1-(3-chloroallyl)-3,5,7-triaza-1-azonia-adamantane chloride;
a carrier comprising a mono-ether capped polyethylene glycol compound or a polypropylene glycol compound; and
a thickener comprising a polyethylene glycol compound.

8. A biocidal composition according to claim 7 comprising:
0.1 to 50% by weight of the 1-(3-chloroallyl)-3,5,7-triaza-1-azonia-adamantane chloride;
0.1 to 40% by weight of the 1,2-benzisothiazolin-3-one;
0.1 to 20% by weight of the dispersant;
0.1 to 10% by weight of the optional thickener; and
balance carrier.

9. A biocidal composition according to claim 1 that is non-aqueous.

10. A method of inhibiting bacterial growth in a medium, the method comprising providing the medium with a biocidal composition according to claim 1.

11. A method according to claim 10 wherein the medium comprises: paints and coatings, emulsion polymers and latexes, surfactants, metal working fluids, cleaners, detergents, household products, agricultural products, or leather products.

* * * * *